US006596773B2

(12) United States Patent
Bös et al.

(10) Patent No.: US 6,596,773 B2
(45) Date of Patent: Jul. 22, 2003

(54) PHENYL SUBSTITUTED PYRIDINE AND BENZENE DERIVATIVES

(75) Inventors: Michael Bös, Montreal (CA); Guido Galley, Rheinfelden (DE); Thierry Godel, Basel (CH); Torsten Hoffmann, Lorrach (DE); Walter Hunkeler, Magden (CH); Patrick Schnider, Oberwil (CH); Heinz Stadler, Rheinfelden (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/051,699

(22) Filed: Jan. 17, 2002

(65) Prior Publication Data

US 2002/0111367 A1 Aug. 15, 2002

Related U.S. Application Data

(62) Division of application No. 09/505,356, filed on Feb. 16, 2000, now Pat. No. 6,407,111.

(30) Foreign Application Priority Data

Feb. 24, 1999 (EP) .............................. 99103502

(51) Int. Cl.$^7$ .................. A61K 31/67; C07C 233/24

(52) U.S. Cl. ....................... 514/617; 564/182

(58) Field of Search .................. 564/182; 514/617

(56) References Cited

U.S. PATENT DOCUMENTS 5,972,938 A 10/1999 Rupniak et al.

FOREIGN PATENT DOCUMENTS

| DE | 10008042 | 8/2000 |
|----|----------|--------|
| EP | 1 103 545 A1 | 5/2001 |
| WO | WO 95/16679 | 6/1995 |
| WO | WO 95/18124 | 7/1995 |
| WO | WO 95/23798 | 9/1995 |
| WO | WO 97/31635 | 9/1997 |
| WO | WO 99/01421 | 1/1999 |
| WO | WO 00/40237 | 7/2000 |
| WO | WO 00/53572 | 9/2000 |

OTHER PUBLICATIONS

Barker, *Reviews in Neuroscience.*, vol. 7(3),pp. 187–214 (1996).
Longmore et al., *Can. J. Physiol.*, vol. 75, pp. 612–621 (1997).
Kramer et al., *Science*, vol. 281, pp. 1640–1645 (1998).
Maggi et al., *J. Auton. Pharmacol.*, vol. 13, pp. 23–93 (1993).
Navari et al., *New England J. of Medicine*, vol. 340(3), pp. 190–195 (1999).
Database Chemabs.No.XP002151988.

*Primary Examiner*—Robert W. Ramsuer
(74) *Attorney, Agent, or Firm*—George W. Johnston; Patricia S. Rocha-Tramaloni; Lyman H. Smith

(57) ABSTRACT

The present invention is a series of compounds formed from phenyl substituted pyridine or benzene derivatives and their pharmaceutically acceptable salts. These compounds have shown high affinity as antagonists to the NK-1 receptor.

7 Claims, No Drawings

PHENYL SUBSTITUTED PYRIDINE AND BENZENE DERIVATIVES

This application is a divisional application of U.S. patent application Ser. No. 09/505,356, filed Feb. 16, 2000 now U.S. Pat. No. 6,407,111.

BACKGROUND OF THE INVENTION

The neuropeptide receptor for Neurokinin 1 (substance P, NK-1) is widely distributed throughout the mammalian nervous system (especially brain and spinal ganglia), the circulatory system and peripheral tissues (especially the duodenum and jejunum) and are involved in regulating a number of diverse biological processes. Substance P is a naturally occurring undecapeptide belonging to the tachykinin family of peptides, the latter being so-named because of their prompt contractile action on extravascular smooth muscle tissue. The receptor for substance P is a member of the superfamily of G protein-coupled receptors.

The central and peripheral actions of the mammalian tachykinin, substance P, have been associated with numerous inflammatory conditions including migraine, rheumatoid arthritis, asthma, and inflammatory bowel disease as well as mediation of the emetic reflex and the modulation of central nervous system (CNS) disorders such as Parkinson's disease (*Neurosci. Res.*, 1996, 7, 187–214), anxiety (*Can. J. Phys.*, 1997, 75, 612–621) and depression (*Science*, 1998, 281, 1640–1645).

Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases is reviewed in "Tachykinin Receptor and Tachykinin Receptor Antagonists", *J. Auton. Pharmacol.*, 13, 23–93, 1993.

Furthermore, Neurokinin 1 receptor antagonists are being developed for the treatment of a number of physiological disorders associated with an excess or imbalance of tachykinin, in particular substance P. Examples of conditions in which substance P has been implicated include disorders of the central nervous system such as anxiety, depression and psychosis (WO 95/16679, WO 95/18124 and WO 95/23798).

The neurokinin-1 receptor antagonists are further useful for the treatment of motion sickness and for treatment induced vomiting.

In addition, in *The New England Journal of Medicine*, Vol. 340, No. 3 190–195, 1999 has been described the reduction of cisplatin-induced emesis by a selective neurokinin-1-receptor antagonist.

Furthermore, U.S. Pat. No. 5,972,938 describes a method for treating a psychoimmunologic or a psychosomatic disorder by administration of a tachykinin receptor, such as NK-1 receptor antagonist.

SUMMARY OF THE INVENTION

In accordance with the present invention, the compounds of formula I and their salts are characterized by valuable therapeutic properties. It has been surprisingly found that the compounds of the present invention are antagonists of the Neurokinin 1 (NK-1, substance P) receptor. Objects of the present invention are the compounds of formula I and pharmaceutically acceptable salts thereof, the preparation of the above-mentioned compounds, medicaments containing them and their manufacture as well as the use of the above-mentioned compounds in the control or prevention of illnesses, especially of illnesses and disorders of the kind referred to earlier or in the manufacture of corresponding medicaments. The most preferred indications for treatment in accordance with the present invention are those which include disorders of the central nervous system or emesis, for example the treatment or prevention of certain depressive disorders by the administration of NK-1 receptor antagonists. A major depressive episode has been defined as being a period of at least two weeks during which, for most of the day and nearly every day, there is either depressed mood or the loss of interest or pleasure in all, or nearly all activities.

DETAILED DESCRIPTION OF THE INVENTION

The present invention relates to compounds of the general formula

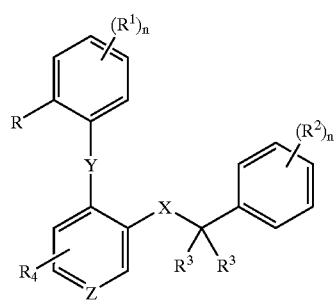

I wherein
  R is hydrogen, lower alkyl, lower alkoxy, halogen or trifluoromethyl;
  $R^1$ is hydrogen or halogen; or
  R and $R^1$ may be together —CH=CH—CH=CH—;
  $R^2$ is hydrogen, halogen, trifluoromethyl, lower alkoxy or cyano;
  $R^3$ is, independently from each other, hydrogen, lower alkyl or form a cycloalkyl group;
  $R^4$ is hydrogen, halogen, lower alkyl, lower alkoxy, —N($R^5$)$_2$, —N($R^5$)S(O)$_2$-lower alkyl, —N($R^5$)C(O)$R^5$ or a cyclic tertiary amine of the group

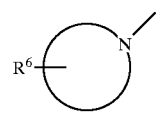

$R^5$ is, independently from each other, hydrogen, $C_{3-6}$-cycloalkyl, benzyl or lower alkyl;
  $R^6$ is hydrogen, hydroxy, lower alkyl, —N($R^5$)CO-lower alkyl, hydroxy-lower alkyl, cyano, —CHO or a 5-or 6 membered heterocyclic group, optionally bonded via an alkylene group,
  X is —C(O)N($R^5$)—, —(CH$_2$)$_m$O—, —(CH$_2$)$_m$N($R^5$)—, —N($R^5$)C(O)—, —C(O)O—or —N($R^5$)(CH$_2$)$_m$—;
  Y is —(CH$_2$)$_n$—, —O—, —S—, —SO$_2$—, —C(O)— or —N($R^5$)—;

Z s=N—, —CH= or —C(Cl)=;

n is 0–4; and m is 1 or 2;

and to pharmaceutically acceptable acid addition salts thereof.

The following definitions of the general terms used in the present description apply irrespective of whether the terms in question appear alone or in combination.

As used herein, the term "lower alkyl" denotes a straight- or branched-chain alkyl group containing from 1–7 carbon atoms, for example, methyl, ethyl, propyl, isopropyl, n-butyl, i-butyl, t-butyl and the like.

Preferred lower alkyl groups are groups with 1–4 carbon atoms.

The term "lower alkoxy" denotes a group wherein the alkyl residues are as defined above, and which is attached via an oxygen atom.

The term "halogen" denotes chlorine, iodine, fluorine and bromine.

The term "cycloalkyl" denotes a saturated carbocyclic group, containing 3–6 carbon atoms.

The term "cyclic tertiary amine" denotes, for example, pyrrol-1-yl, imidazol-1-yl, piperidin-1-yl, piperazin-1-yl, morpholin-4-yl, thiomorpholin-4-yl, 1-oxo-thiomorpholin-4-yl or 1,1-dioxo-thiomorpholin-4-yl.

The term "5 or 6 membered heterocyclic group" denotes, for example pyridinyl, pyrimidinyl, oxadiazolyl, triazolyl, tetrazolyl, thiazolyl, thienyl, furyl, pyranyl, pyrrolyl, imidazolyl, pyrazolyl, isothiazolyl, piperazinyl or piperidyl.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

Exemplary preferred are compounds, in which Y is —C(O)— and $R^4$ is 4-methylpiperazinyl, for example the following compounds:

N-[2-Benzoyl-4-(4-methyl-piperazin-1-yl)-phenyl]-2-(3,5-bis-trifluoromethyl-phenyl)isobutyramide, 4-Benzoyl-N-(3,5-bis-trifluoromethyl-benzyl)-N-methyl-6-(4-methyl-piperazin-1-yl)-nicotinamide and N-(3,5-Bis-trifluoromethyl-benzyl)-4-(2-chloro-benzoyl)-N-methyl-6-(4-methyl-piperazin-1-yl) nicotinamide.

Further preferred are compounds, in which Y is —O— and $R^4$ is hydrogen, morpholinyl or 4-methylpiperazinyl. Examples of such compounds are:

2-(3,5-Bis-trifluoromethyl-phenyl)-N-methyl-N-(2-phenoxy-phenyl)-isobutyramide, 2-(3,5-Bis-trifluoromethyl-phenyl)-N-methyl-N-(2-o-tolyloxy-phenyl)-isobutyramide, 2-(3,5-Bis-trifluoromethyl-phenyl)-N-[2-(2,4-dichloro-phenoxy)-phenyl]-N-methyl-isobutyramide, N-(3,5-Bis-trifluoromethyl-benzyl)-N-methyl-6-morpholin-4-yl-4-phenoxy-nicotinamide, N-(3,5-Bis-trifluoromethyl-benzyl)-4-(2-chloro-phenoxy)-N-methyl-6-morpholin-4-yl-nicotinamide, N-(3,5-Bis-trifluoromethyl-benzyl)-4-(2-chloro-phenoxy)-N-methyl-6-(4-methyl-piperazin-1-yl)-nicotinamide and N-(3,5-Bis-trifluoromethyl-benzyl)-N-methyl-6-morpholin-4-yl-4-o-tolyloxy-nicotinamide.

Further preferred are compounds, in which Y is —N(CH$_3$)— and $R^4$ is hydrogen, for example the following compounds:

2-(3,5-Bis-trifluoromethyl-phenyl)-N-methyl-N-[2-(methyl-phenyl-amino)-phenyl]-propionamide, 2-(3,5-Bis-trifluoromethyl-phenyl)-N-methyl-N-[2-(methyl-phenyl-amino)-phenyl]-isobutyramide, 2-(3,5-B is-trifluoromethy l-phenyl)-N-[2-(methyl-phenyl-amino)-phenyl]-acetamide and 2-(3,5-Bis-trifluoromethyl-phenyl)-N-methyl-N-[2-(methyl-phenyl-amino)-phenyl]-acetamide.

The present compounds of formula I and their pharmaceutically acceptable salts can be prepared by methods known in the art, for example, by processes described below, which process comprises reacting a compound of formula

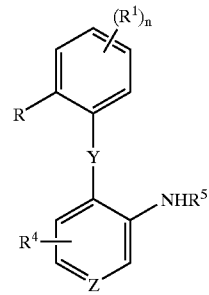

II with a compound of formula

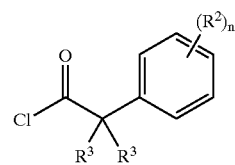

III to a compound of formula

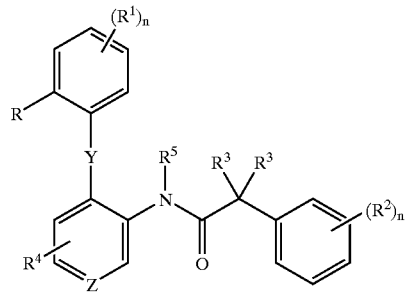

I-1 wherein $R^1$–$R^5$, R, Y, Z and n have the significances given above, or b) reacting a compound of formula

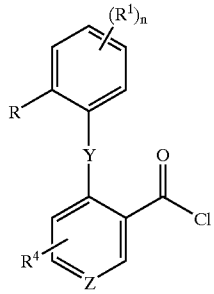

IV with a compound of formula

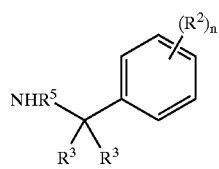

V to give a compound of formula

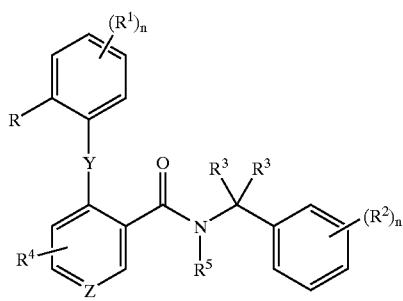

I-2 wherein $R^1$–$R^5$, R, Z, Y and n have the significances given above, or reducing a compound of formula

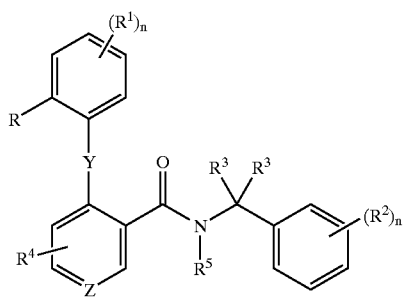

I-2 to a compound of formula

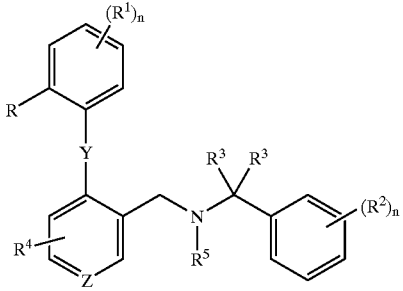

I-4 wherein the definitions of substituents are given above, or d) reacting a compound of formula

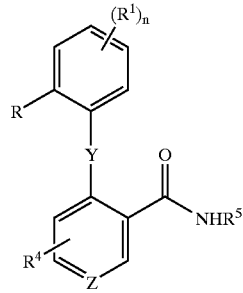

VI with a compound of formula

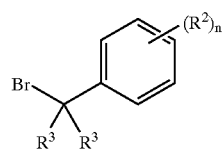

VII to a compound of formula

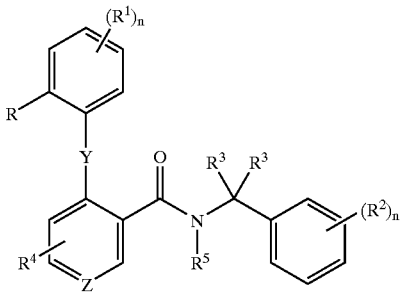

I-2 wherein the definitions of substituents are given above, or e) reacting a compound of formula

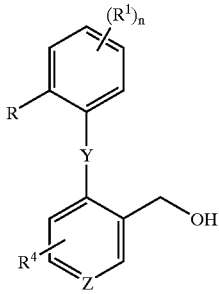

with a compound of formula

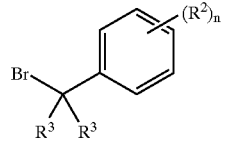

to a compound of formula

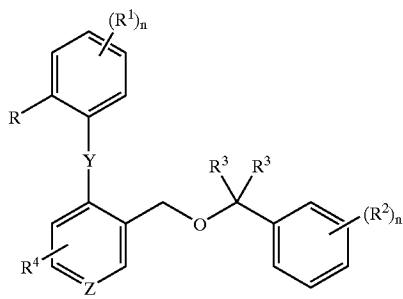

wherein the definitions of substituents are given above, or f) reducing a compound of formula

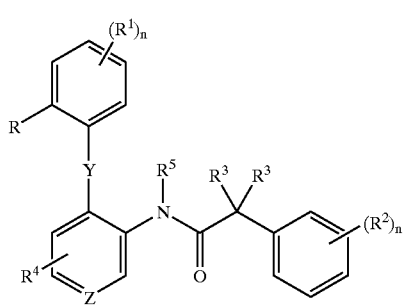

to a compound of formula

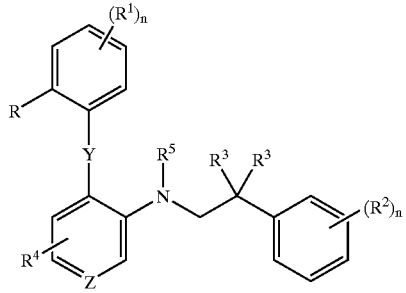

wherein the definitions of substituents are given above, or g) reacting a compound of formula

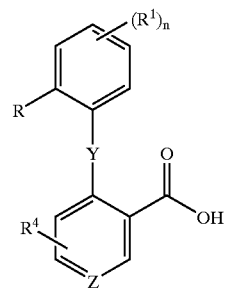

with a compound of formula

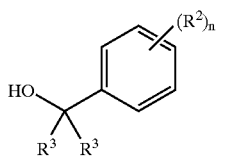

to a compound of formula

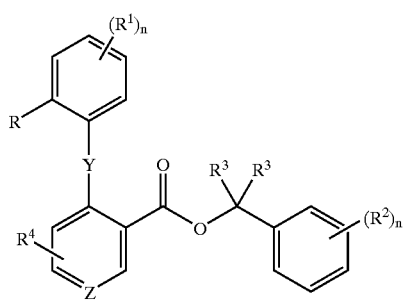

wherein the definition of substituents is given above, or
h) reacting a compound of formula

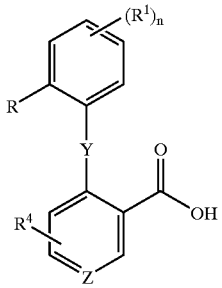

with a compound of formula

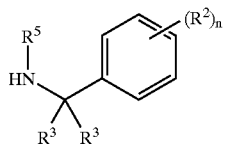

to a compound of formula

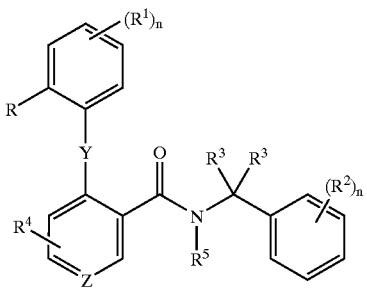

wherein the definition of substituents is given above, or
i) reacting a compound of formula

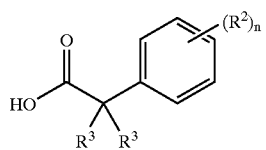

with a compound of formula

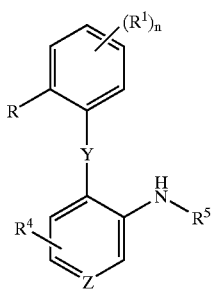

to a compound of formula

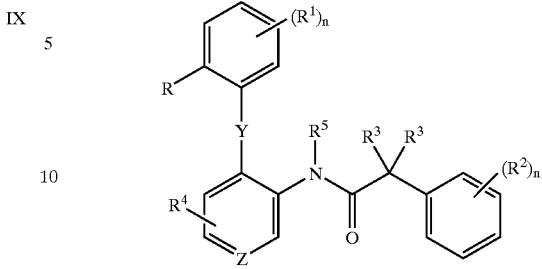

wherein the definition of substituents is given above, or
j) modifying one or more substituents $R^1$–$R^5$ or R within the definitions given above, and
if desired, converting the compound obtained into a pharmaceutically acceptable acid addition salt.

In accordance with process variant a) a compound of formula II, for example 3-amino-4-benzoylpyridine, is cooled in an ice bath and a compound of formula III, for example 2-(3,5-bis-trifluoromethyl-phenyl)-2-methyl propionyl chloride in the presence of DIPEA (N-ethyldiisopropyl-amine) in dichloromethane is added, and then the mixture is stirred at room temperature. The desired compound of formula I-1 is yielded after purification in good yields.

Process variant b) describes the reaction of a compound of formula IV with a compound of formula V to a compound of formula I-2. The reaction is carried out in conventional manner, for example in a solvent, such as a mixture of toluene and triethyl-amine. The mixture is refluxed for about 1 hour.

In accordance with process variant c) a compound of formula I-2 is reduced to a compound of formula I-4. This reaction is carried out with a reducing agent, such as LiAlH4 or BH3.THF, in conventional manner.

Process variant d) describes the reaction of a compound of formula VI with a compound of formula VII to a compound of formula I-2. This reaction is carried out by deprotonation of a compound of formula VI with KHMDS (potassium hexamethyldisilazide) and subsequent addition of a compound of formula VII. A suitable solvent is tetra-hydrofuran. The reaction is carried out at room temperature.

In accordance with process variant e) a compound of formula I-5 is prepared. This reaction is carried out by deprotonation of a compound of formula VIII with NaH and subsequent addition of a compound of formula VII. This reaction is carried out in conventional manner.

A further method for the preparation of a compound of formula I is described in process variant f). A compound of formula I-1 is reduced to a compound of formula I-3 in conventional manner, for example with LiAlH4 or BH$_3$.THF.

In the process variant g) a compound of formula IX is activated with DCC (N,N'-dicyclohexylcarbodiimide) and DMAP (4-N,N-dimethylaminopyridine). Subsequent addition of a compound of formula X yields a compound of formula I-6.

In accordance with variant h) a compound of formula IX is activated with CDI (1,1'-carbonyldiimidazole) and subsequent addition of a compound of formula V gives a compound of formula I-2.

The process variant i) describes the process for preparation of a compound of formula I-1, wherein a compound of formula XII is activated with CDI and subsequent addition of a compound of formula II yields a compound of formula I-13.

The salt formation is effected at room temperature in accordance with methods which are known per se and which are familiar to any person skilled in the art. Not only salts with inorganic acids, but also salts with organic acids came into consideration. Hydrochlorides, hydrobromides, sulphates, nitrates, citrates, acetates, maleates, succinates, methan-sulphonates, p-toluenesulphonates and the like are examples of such salts.

The following schemes 1–7 describe the processes for preparation of compounds of formula I in more detail. The starting materials of formulae IX, X, XI, II, III, XII, XIII, XV, XVII, XVIII, XX, XXII, XXIV and XXV are known compounds or may be prepared according to methods known in the art.

In the schemes the following abbreviations have been used:

| | |
|---|---|
| DCC | N,N'-dicyclohexylcarbodiimide |
| DMAP | 4-(N,N-dimethylamino)pyridine |
| CDI | 1,1'-carbonyldiimidazole |
| KHMDS | potassium hexamethyldisilazide |
| DIPEA | N-ethyldiisopropyl-amine |
| PivCl | pivaloyl chloride |

Scheme 1

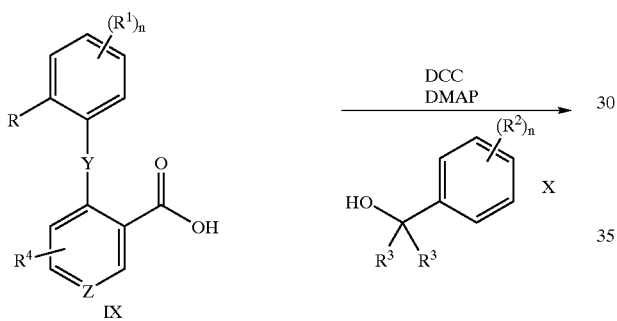

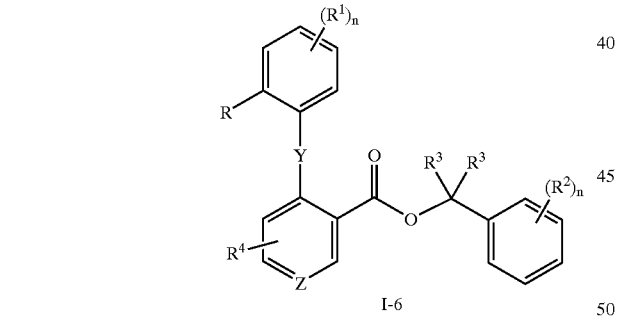

The substituents are given above.

Scheme 2

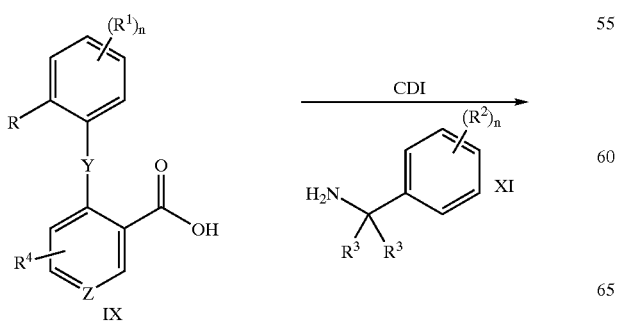

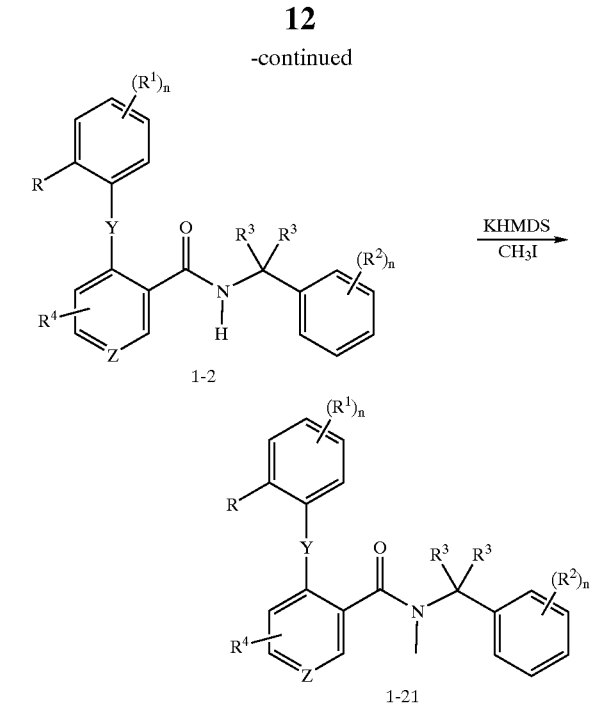

The substituents are given above.

Scheme 3

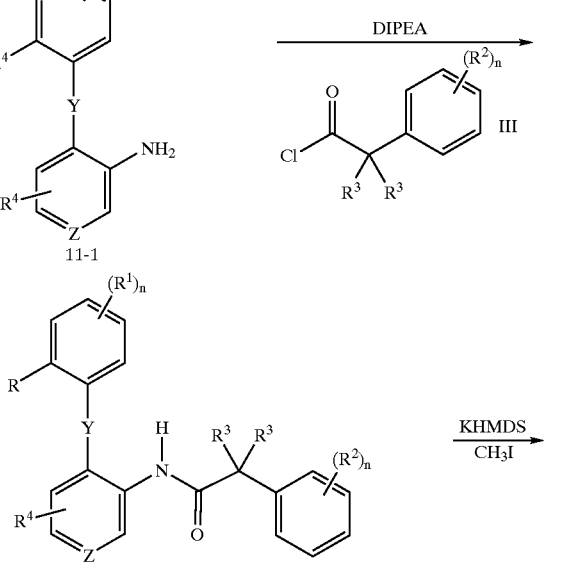

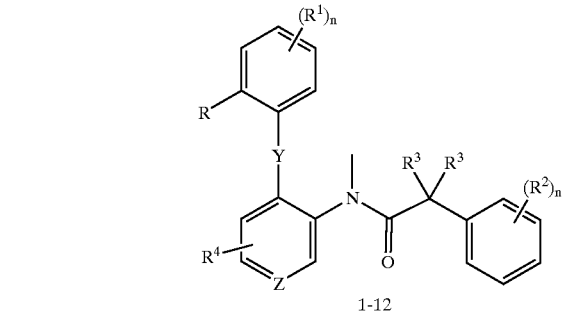

The definition of substituents is given above.
Scheme 4
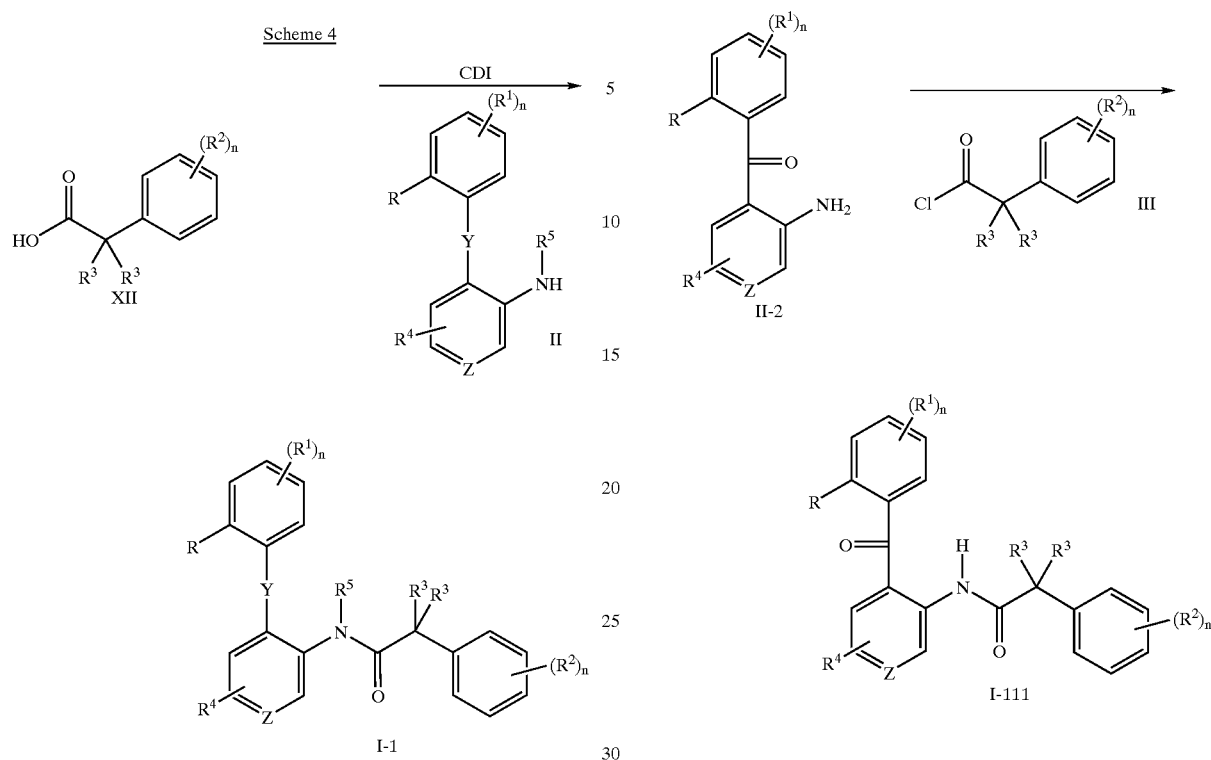
The definition of substituents is given above.
Scheme 5
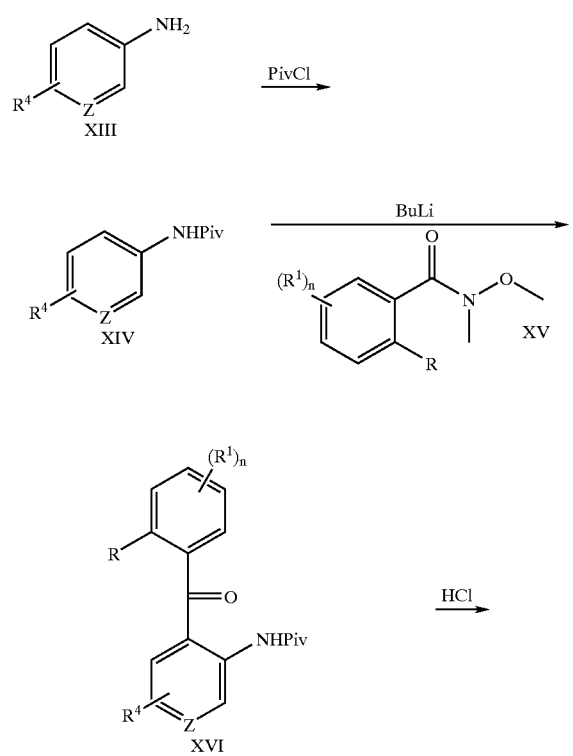
Scheme 6
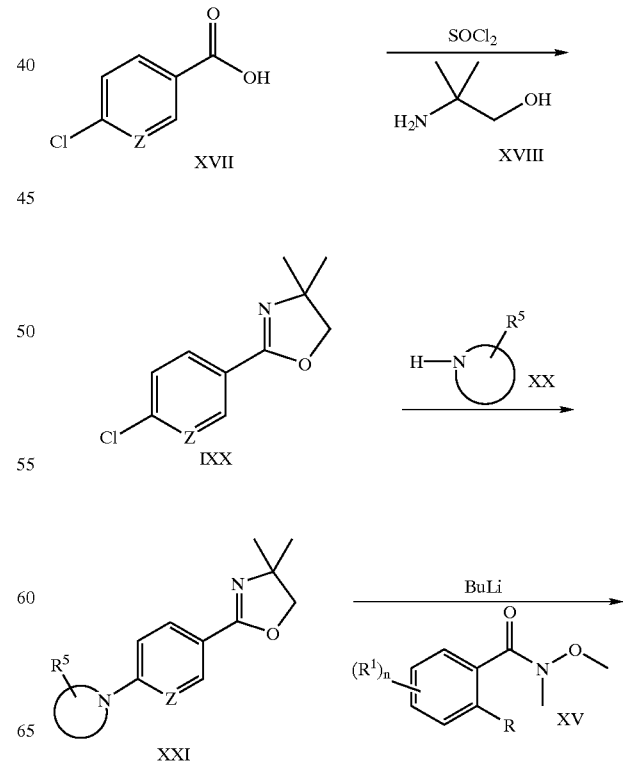

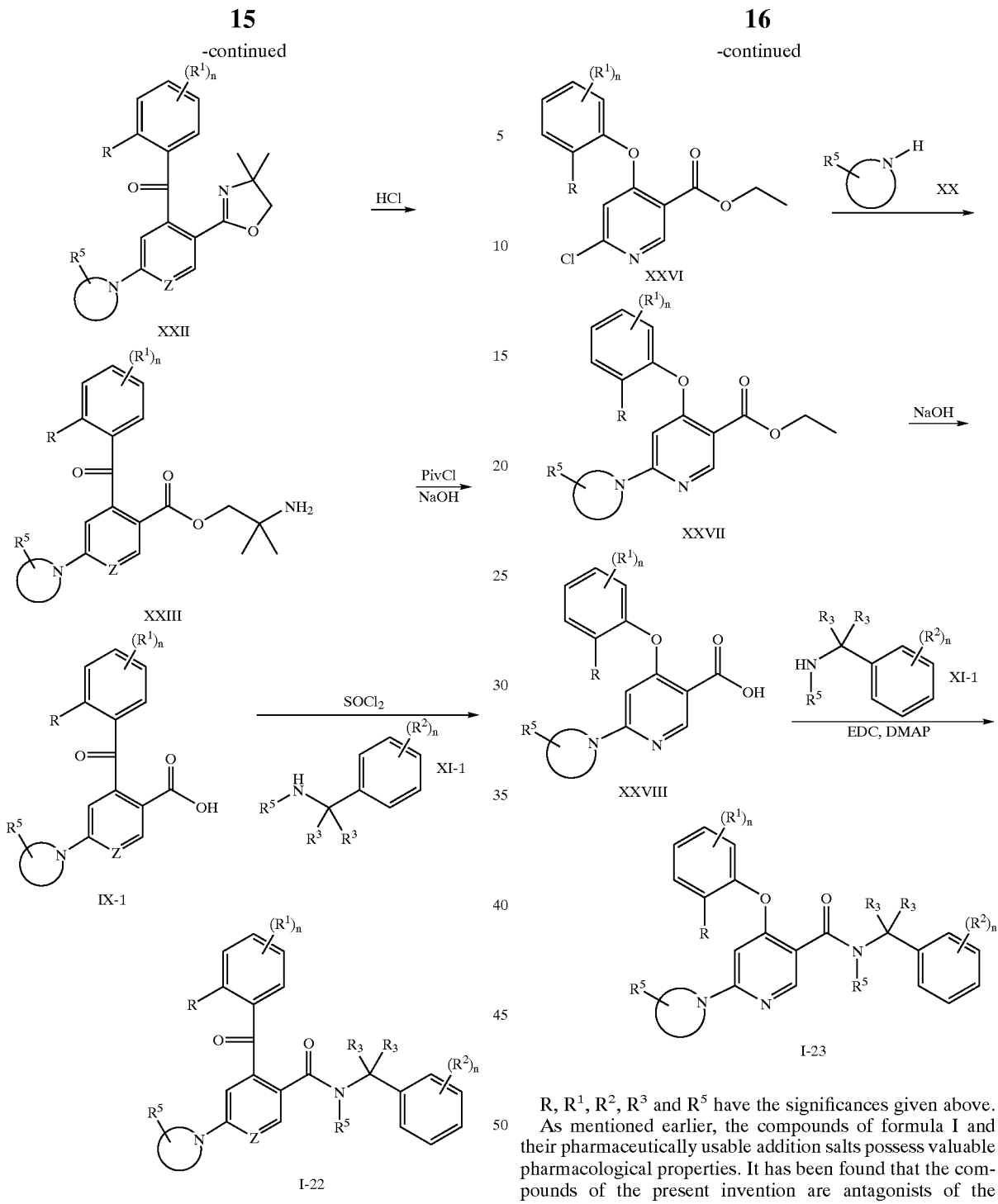

The definition of substituents is given above.

Scheme 7

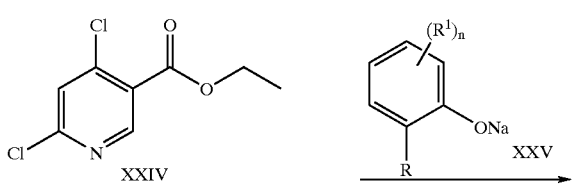

R, $R^1$, $R^2$, $R^3$ and $R^5$ have the significances given above.

As mentioned earlier, the compounds of formula I and their pharmaceutically usable addition salts possess valuable pharmacological properties. It has been found that the compounds of the present invention are antagonists of the Neurokinin 1 (NK-1, substance P) receptor.

The compounds were investigated in accordance with the tests given hereinafter.

The affinity of test compounds for the NK1 receptor was evaluated at human NK1 receptors in CHO cells infected with the human NK1 receptor (using the Semliki virus expression system) and radiolabelled with [3H]substance P (final concentration 0.6 nM). Binding assays were performed in HEPES buffer (50 mM, pH 7.4) containing BSA (0.04%) leupeptin (8 mg/ml), MnCl2 (3 mM) and phosphoramidon (2 mM). Binding assays consisted of 250 ml of membrane suspension (1.25×105 cells/assay tube), 0.125 ml of buffer of displacing agent and 125 ml of [3H]substance P. Displacement curves were determined with at least seven concentrations of the compound. The assay tubes were incubated for 60 min at room temperature after which time the tube contents were rapidly filtered under vacuum through GF/C filters presoaked for 60 min with PEI (0.3%) with 2×2 ml washed of HEPES buffer (50 mM, pH 7.4). The radioactivity retained on the filters was measured by scintillation counting. All assays were performed in triplicate in at least 2 separate experiments.

The affinity to the NK-1 receptor, given as pKi, is in the scope of 7,50–9,00 for the preferred compounds. Examples for such compounds are

| | |
|---|---|
| N-(3,5-Bis-trifluoromethyl-benzyl)-N-methyl-6-morpholin-4-yl-4-phenoxy-nicotinamide | 7,86 |
| N-(3,5-Bis-trifluoromethyl-benzyl)-4-(2-chloro-phenoxy)-N-methyl-6-(4-methyl-piperazin-1-yl)-nicotinamide | 8,42 |
| N-(3,5-Bis-trifluoromethyl-benzyl)-N-methyl-6-morpholin-4-yl-4-o-tolyloxy-nicotinamide | 8,56 |
| N-(3,5-Bis-trifluoromethyl-benzyl)-4-(2-chloro-phenoxy)-N-methyl-6-morpholin-4-yl-nicotinamide | 8,76 |

The compounds of formula I as well as their pharmaceutically usable acid addition salts can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The compounds of formula I and their pharmaceutically usable acid addition salts can be processed with pharmaceutically inert, inorganic or organic excipients for the production of tablets, coated tablets, dragees and hard gelatine capsules. Lactose, corn starch or derivatives thereof, talc, stearic acid or its salts etc can be used as such excipients e.g. for tablets, dragées and hard gelatine capsules. Suitable excipients for soft gelatine capsules are e.g. vegetable oils, waxes, fats, semisolid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

The following Examples illustrate the present invention without limiting it. All temperatures are given in degrees Celsius.

EXAMPLE 1

N-(4-Benzoyl-pyridin-3-yl)-2-(3,5-bis-trifluoromethyl-phenyl)-N-methyl-isobutyramide a) N-(4-Benzoyl-pyridin-3-yl)-2-(3,5-bis-trifluoromethyl-phenyl)-isobutyramide A solution of 397 mg (2 mmol) 3-amino-4-benzoylpyridine and 517 mg (4 mmol) N-ethyldiisopropylamine in 8 ml dichloromethane was cooled in an ice bath and a solution of 765 mg (2.4 mmol) 2-(3,5-bis-trifluoromethyl-phenyl)-2-methyl-propionyl chloride in 8 ml dichloromethane was added dropwise. The reaction mixture was warmed to room temperature and was stirred overnight. Water (5 ml) was added and the organic layer was separated. The aqueous phase was extracted with dichloromethane. The combined organic layers were dried (magnesium sulfate) and evaporated. The residue was purified by flash chromatography to give 235 mg (24%) of the title compound as orange oil.

MS m/e (%): 481.3 (M+H$^+$, 100).

b) N-(2-Benzoyl-4-chloro-phenyl)-2-(3,5-bis-trifluoromethyl-phenyl)-N-methyl-isobutyramide To a solution of 96 mg (0.2 mmol) of N-(4-benzoyl-pyridin-3-yl)-2-(3,5-bis-trifluoromethyl-phenyl)-isobutyramide in 1.2 ml of dimethylformamide were added 0.22 ml of a 1M potassium hexamethyldisilazide solution at 0° C. After 30 min 57 mg of methyl iodide (0.4 mmol) were added and the reaction mixture was stirred at room temperature overnight. The solvent was evaporated, water and dichloromethane were added to the residue, the organic layer was separated and dried over magnesium sulfate. After evaporation of the solvent the product was purified by flash chromatography to yield 12 mg (12%) of the title compound as yellow oil.

MS m/e (%): 495.2 (M+H$^+$, 100).

EXAMPLE 2

N-(2-Benzoyl-4-chloro-phenyl)-2-(3,5-bis-trifluoromethyl-phenyl)-N-methyl-isobutyramide a) N-(2-Benzoyl-4-chloro-phenyl)-2-(3,5-bis-trifluoromethyl-phenyl)-isobutyramide To a solution of 233 mg (1 mmol) of 2-amino-5-chlorobenzophenone in 2 ml of 1,2-dichloroethane were added 360 mg (1.2 mmol) of 2-(3,5-bis-trifluoromethyl-phenyl)-2-methyl-propionic acid and the reaction mixture was shaken at 80° C. for 1 h. Dicyclohexyl carbodiimide (194 mg, 1.2 mmol) was added and shaking was continued overnight at the same temperature. The solvent was evaporated and the residue obtained was purified by column chromatography on silica gel to yield 298 mg (58%) of the title compound as yellow oil.

MS m/e (%): 514.2 (M+H$^+$, 100)

b) N-(2-Benzoyl-4-chloro-phenyl)-2-(3,5-bis-trifluoromethyl-phenyl)-N-methyl-isobutyramide To a solution of 154 mg (0.3 mmol) of N-(2-benzoyl-4-chloro-phenyl)-2-(3,5-bis-trifluoromethyl-phenyl)-isobutyramide in 1 ml dimethylformamide were added 26 mg (0.6 mmol) sodium hydride (55% suspension in mineral oil). After 30 min stirring at room temperature 85 mg of methyl iodide (0.6 mmol) were added and the reaction mixture was stirred at 80° C. overnight. The solvent was evaporated under reduced pressure and the residue was purified by flash chromatography to yield 51 mg (32%) of the title compound as white crystals. M.p. 89–91° C.

MS m/e (%): 528.1 (M+H$^+$, 100).

EXAMPLE 3
N-(2-Benzoyl-5-chloro-phenyl)-2-(3,5-bis-trifluoromethyl-phenyl)-N-methyl-isobutyramide The title compound was obtained as yellow oil in comparable yields according to the procedures described above for the preparation of N-(2-benzoyl-4-chloro-phenyl)-2-(3,5-bis-trifluoromethyl-phenyl)-N-methyl-isobutyramide using 2-amino-4-chlorobenzophenone instead of 2-amino-5-chlorobenzophenone.

MS m/e (%): 528.1 (M+H$^+$, 100).

EXAMPLE 4
N-(2-Benzoyl-3-chloro-phenyl)-2-(3,5-bis-trifluoromethyl-phenyl)-N-methyl-isobutyramide The title compound was obtained as yellowish oil in comparable yields according to the procedures described above for the preparation of N-(2-benzoyl-4-chloro-phenyl)-2-(3,5-bis-trifluoromethyl-phenyl)-N-methyl-isobutyramide using 2-amino-6-chlorobenzophenone instead of 2-amino-5-chlorobenzophenone.

MS m/e (%): 528.1 (M+H$^+$, 100).

EXAMPLE 5
2-(3,5-Bis-trifluoromethyl-phenyl)-N-[2-(3-chloro-benzoyl)-phenyl]-N-methyl-isobutyramide The title compound was obtained as yellow oil in comparable yields according to the procedures described above for the preparation of N-(2-benzoyl-4-chloro-phenyl)-2-(3,5-bis-trifluoromethyl-phenyl)-N-methyl-isobutyramide using 2-(3-chlorobenzoyl)-aniline instead of 2-amino-5-chlorobenzophenone.

MS m/e (%): 528.1 (M+H$^+$, 100).

EXAMPLE 6
N-(2-Benzoyl-6-methoxy-phenyl)-2-(3,5-bis-trifluoromethyl-phenyl)-N-methyl-isobutyramide The title compound was obtained as yellow oil in comparable yields according to the procedures described above for the preparation of N-(2-benzoyl-4-chloro-phenyl)-2-(3,5-bis-trifluoromethyl-phenyl)-N-methyl-isobutyramide using 2-amino-3-methoxybenzophenone instead of 2-amino-5-chlorobenzophenone.

MS m/e (%): 523.5 (M+H$^+$, 100).

EXAMPLE 7
N-(2-Benzoyl-4-methoxy-phenyl)-2-(3,5-bis-trifluoromethyl-phenyl)-N-methyl-isobutyramide The title compound was obtained as yellow oil in comparable yields according to the procedures described above for the preparation of N-(2-benzoyl-4-chloro-phenyl)-2-(3,5-bis-trifluoromethyl-phenyl)-N-methyl-isobutyramide using 2-amino-5-methoxybenzophenone instead of 2-amino-5-chlorobenzophenone.

MS m/e (%): 523.5 (M+H$^+$, 100).

EXAMPLE 8
(RS)-2-(3,5-Bis-trifluoromethyl-phenyl)-N-[4-chloro-2-(2-chloro-phenylsulfanyl)-phenyl]-N-methyl-propionamide To a solution of 142 mg (0.5 mmol) of 1-chloro-4-methylamino-3-(2-chloro-phenylsulfanyl)-benzene in 2 ml of 1,2-dichloroethane were added 172 mg (0.6 mmol) of 2-(3,5-bis-trifluoromethyl-phenyl)-propionic acid and the reaction mixture was shaken at 80° C. for 1 h. Dicyclohexyl carbodiimide (97 mg, 0.6 mmol) was added and shaking was continued overnight at the same temperature. The solvent was evaporated and the residue obtained was purified by column chromatography on silica gel to yield 56 mg (20%) of the title compound as light yellow oil.

MS m/e (%): 551.9 (M+H$^+$, 100), 553.9 (M+H$^+$, 90).

EXAMPLE 9
(RS)-N-(2-Benzoyl-4-chloro-phenyl)-2-(3,5-bis-trifluoromethyl-phenyl)-N-methyl-propionamide The title compound was obtained as yellow oil in comparable yields according to the procedures described above for the preparation of (RS)-2-(3,5-bis-trifluoromethyl-phenyl)-N-[4-chloro-2-(2-chloro-phenylsulfanyl)-phenyl]-N-methyl-propionamide using 2-methylamino-5-chlorobenzophenone instead of 1-chloro-4-methylamino-3-(2-chloro-phenylsulfanyl)-benzene.

MS m/e (%): 514.2 (M+H$^+$, 100).

EXAMPLE 10
N-[2-Benzoyl-4-(4-methyl-piperazin-1-yl)-phenyl]-2-(3,5-bis-trifluoromethyl-phenyl)-isobutyramide Hydrochloride (1:1)

a) 2,2-Dimethyl-N-[4-(4-methyl-piperazin-1-yl)-phenyl]-propionamide

A solution of 5.58 g (29 mmol) 1-(4-aminophenyl)-4-methylpiperazine and 3.77 g (29 mmol) N-ethyldiisopropylamine in 30 ml tetrahydrofuran was cooled in an ice bath and 3.518 g (29 mmol) pivaloyl chloride were added dropwise. The suspension was stirred for 18 h at room temperature. Water (30 ml) and dichloromethane (50 ml) were added and the organic layer was separated. The aqueous phase was re-extracted with dichloromethane. The combined organic layers were dried (magnesium sulfate) and evaporated to give a white solid. Washing with a mixture of hexane and ethyl acetate (4:1) yielded 6.69 g (83%) of a white crystalline compound.

MS m/e (%): 276.3 (M+H$^+$, 100).

b) N-[2-Benzoyl-4-(4-methyl-piperazin-1-yl)-phenyl]-2,2-dimethyl-propionamide

A solution of 1.375 g (5 mmol) of 2,2-dimethyl-N-[4-(4-methyl-piperazin-1-yl)-phenyl]-propionamide was dissolved in 25 ml tetrahydrofuran and cooled to −70° C. Under argon 7.8 ml (12.5 mmol) of a 1.6 M n-butyl lithium solution in hexane was added slowly at this temperature. The cooling bath was removed and the mixture was stirred for 3 h at room temperature. The reaction mixture was cooled down again to −70° C. and a solution of 1.234 g N-methoxy-N-methyl benzamide (7.2 mmol) in 5 ml tetrahydrofuran was added slowly at −70° C. After 10 min the cooling bath was removed and stirring was continued at room temperature for 1 hour. Water (50 ml) was added to quench the reaction and the mixture was extracted with diethylether (three times 50 ml). The organic layer was dried with magnesium sulfate and evaporated to give a brown oil, which was purified by flash chromatography with dichloromethane/methanol to yield 315 mg (17%)of the product as a light orange solid.

MS m/e (%): 380.4 (M+H$^+$, 100).

c) [2-Amino-5-(4-methyl-piperazin-1-yl)-phenyl]-phenyl-methanone

A solution of 0.3 g (0.8 mmol) of N-[2-benzoyl-4-(4-methyl-piperazin-1-yl)-phenyl]-2,2-dimethyl-propionamide in 10 ml of 3 N aqueous hydrochloric acid was stirred for 20 h at room temperature. The reaction mixture was extracted once with ethyl acetate, the aqueous layer was made alkaline with concentrated sodium hydroxide solution and was extracted four times with dichloromethane. The combined organic layers were dried over magnesium sulfate and evaporated to yield 245 mg (quantitative) of the product as light yellow oil.

MS m/e (%): 296.4 (M+H$^+$, 100).

d) N-[2-Benzoyl-4-(4-methyl-piperazin-1-yl)-phenyl]-2-(3,5-bis-trifluoromethyl-phenyl)-isobutyramide Hydrochloride A solution of 200 mg (0.68 mmol) [2-amino-5-(4-methyl-piperazin-1-yl)-phenyl]-phenyl-methanone and 219 mg (1.69 mmol) N-ethyldiisopropylamine in 5 ml dichloromethane was cooled in an ice bath and a solution of 319 mg (1.0 mmol) 2-(3,5-bis-trifluoromethyl-phenyl)-2-methyl-propionyl chloride in 2 ml dichloromethane was added dropwise. The reaction mixture was warmed to room temperature and was stirred for 3 hours. Water (5 ml) was added and the layers were separated. The aqueous phase was re-extracted with dichloromethane. The combined organic layers were dried (magnesium sulfate) and evaporated to give 50 mg of an oil. The residue was dissolved in 2 ml of ethyl acetate and 0.018 ml of a 4.75 N solution of hydrochloric acid in ethanol was added. After addition of 1 ml of diethylether the suspension was stirred for 15 min, the solid was filtered off and dried to give 24 mg (6%) of the title compound as a white solid.

MS m/e (%): 578.1 (M+H$^+$, 100).

EXAMPLE 11

4-Benzoyl-N-(3,5-bis-trifluoromethyl-benzyl)-N-methyl-6-(4-methyl-piperazin-1-yl)-nicotinamide Hydrochloride (1:1)

a) 2-Chloro-5-(4,4-dimethyl-4,5-dihydro-oxazol-2-yl)-pyridine Hydrochloride

To 10 g (63.47 mmol) 2-chloropyridine-5-carboxylic acid were added 60 g (507 mmol) thionylchloride and the mixture was refluxed for 3 h. Excess thionylchloride was distilled off, ether (50 ml) was added and evaporated to remove traces of thionylchloride. The residue was dissolved in 30 ml dichloromethane and added dropwise to a solution of 11.88 g (0.133 mmol) 2-amino-2-methylpropanol in 30 ml dichloromethane at 0° C. The reaction mixture was stirred for 2 hours at room temperature and 30 ml water were added. The layers were separated and the aqueous phase was extracted again with dichloromethane. The combined organic layers were dried with magnesium sulfate and evaporated to yield an oily liquid. To the residue were added 22.6 g (190 mmol) of thionylchloride at 0° C. and the mixture was stirred for 30 min. Ethyl acetate was added, the mixture was stirred for another 30 min and the crystals were washed with ethyl acetate and ether to yield 14 g (89%) of a white solid.

MS m/e (%): 210 (M+H$^+$, 10).

b) 1-[5-(4,4-Dimethyl-4,5-dihydro-oxazol-2-yl)-pyridin-2-yl]-4-methyl-piperazine 2-Chloro-5-(4,4-dimethyl-4,5-dihydro-oxazol-2-yl)-pyridine hydrochloride was transformed into its free base by dissolving 8.0 g (32 mmol) in saturated sodium bicarbonate solution and extracting the base into dichloromethane. The solvent was evaporated and the residue was dissolved in toluene. After addition of 11.35 g (113 mmol) N-methylpiperazine, the mixture was refluxed for 36 h. After cooling to room temperature water (50 ml) and ethyl acetate (150 ml) were added and the aqueous layer was extracted with ethyl acetate (150 ml). The combined organic layers were extracted two times with 1 N hydrochloric acid, the acidic aqueous layer was made alkaline with 28% sodium hydroxide solution and extracted two times with dichloromethane. The organic layer was dried (magnesium sulfate) and evaporated. The residue was crystallized from ethyl acetate/hexane to yield 6.0 g (67%) of a white crystalline compound.

MS m/e (%): 274.1 (M+H$^+$, 100).

c) [5-(4,4-Dimethyl-4,5-dihydro-oxazol-2-yl)-2-(4-methyl-piperazin-1-yl)-pyridin-4-yl]-phenyl-methanone 2,2,6,6-Tetramethylpiperidine (0.932 g, 6.6 mmol) was placed in a three-necked flask. Under argon 10 ml of hexane were added, the solution was cooled to 0° C. and n-butyl lithium (1.6 M solution in hexane) was added slowly. After stirring the yellow suspension for 10 min at 0° C., N,N,N',N'-tetramethylethylenediamine (767 mg, 6.6 mmol) was added. This mixture was added dropwise to a suspension of 1.65 g (6 mmol) of 1-[5-(4,4-dimethyl-4,5-dihydro-oxazol-2-yl)-pyridin-2-yl]-4-methyl-piperazine in 20 ml of hexane at −78°. After stirring the yellow solution for 30 min at this temperature and for 45 min at 0° C., a solution of 1.19 g N-methoxy-N-methyl benzamide (7.2 mmol) in 2 ml hexane/2 ml tetrahydrofuran was added slowly at 0° C. After 30 min, the cooling bath was removed and stirring was continued at room temperature overnight. Water was added and the mixture was extracted with ethyl acetate. The organic layer was dried (magnesium sulfate) and evaporated to give a brown oil, which was purified by flash chromatography with dichloromethane/methanol to yield 1.16 g (51%) of the product as a yellow solid.

MS m/e (%): 379.5 (M+H$^+$, 100).

d) 4-Benzoyl-6-(4-methyl-piperazin-1-yl)-nicotinic acid 2-amino-2-methyl-propyl Ester To a solution of 1.13 g (3 mmol) [5-(4,4-dimethyl-4,5-dihydro-oxazol-2-yl)-2-(4-methyl-piperazin-1-yl)-pyridin-4-yl]-phenyl-methanone in 30 ml tetrahydrofuran were added 3 ml of 2 N aqueous hydrochloric acid and the reaction mixture was heated at 50° C. for 18 h. After cooling to room temperature, 1 N sodium hydroxide solution was added to adjust pH 11 and the mixture was extracted with ethyl acetate. The organic layer was dried (magnesium sulfate) and evaporated to yield 1.18 g (quantitative) of the product as yellow oil.

MS m/e (%): 481.4 (M+H$^+$, 100).

e) 4-Benzoyl-6-(4-methyl-piperazin-1-yl)-nicotinic Acid

To a solution of 1.15 g (2.9 mmol) of 4-benzoyl-6-(4-methyl-piperazin-1-yl)-nicotinic acid 2-amino-2-methylpropyl ester in 20 ml tetrahydrofuran were added dropwise 367 mg (3.05 mmol) pivaloyl chloride at 0° C. After stirring the light yellow suspension at the same temperature for 1 hour, 1 M aqueous hydrochloric acid was added. Excess pivaloyl chloride was extracted with dichloromethane, the aqueous layer was made alkaline with 28% sodium hydroxide solution and extracted twice with dichloromethane. The organic layer was dried (magnesium sulfate) and evaporated. The residue was dissolved in methanol, 1 M aqueous sodium hydroxide solution was added slowly at 0° C. and the mixture was heated overnight at 65° C. Methanol was evaporated and the aqueous layer was adjusted to pH 5. The solvent was evaporated to yield the product contaminated with sodium chloride, which was used for the next step without further purification.

f) 4-Benzoyl-N-(3,5-bis-trifluoromethyl-benzyl)-N-methyl-6-(4-methyl-piperazin-1-yl)-nicotinamide Hydrochloride (1:1)

A mixture of 4-benzoyl-6-(4-methyl-piperazin-1-yl)-nicotinic acid (1.5 mmol) from the last step and 3 ml of thionyl chloride were heated to 110° C. for 1 hour. Excess of thionyl chloride was evaporated, the brown oil obtained was re-dissolved in ether and evaporated again to remove traces of thionyl chloride. The residue was dissolved in 2 ml of acetone and 1.16 g (4.5 mmol) (3,5-bis-trifluoromethylbenzyl)-methyl-amine were added. The mixture was stirred for 1.5 h at room temperature. The solvent was evaporated, dichloromethane and water were added and the aqueous layer was made alkaline with sodium hydroxide solution (28%). The organic layer was dried (magnesium sulfate), evaporated and purified by flash chromatography to yield 202 mg of an oil. This compound was dissolved in 5 ml diethyl ether and 0.075 ml of 4.75 N hydrochloric acid solution in ethanol were added. After stirring for 15 min the suspension was evaporated to dryness, re-suspended in 10 ml diethyl ether, filtered and dried to give 190 mg (21%) of the title compound as a white solid. M.p. 105° C., (decomp.).

MS m/e (%): 565.2 (M+H$^+$, 100).

EXAMPLE 12

N-(3,5-Bis-trifluoromethyl-benzyl)-4-(2-chloro-benzoyl)-N-methyl-6-(4-methyl-piperazin-1-yl)-nicotinamide Hydrochloride (1:1)

The title compound was obtained as white crystals in comparable yields according to the procedures described above for the preparation of 4-benzoyl-N-(3,5-bis-trifluoromethyl-benzyl)-N-methyl-6-(4-methyl-piperazin-1-yl)-nicotinamide hydrochloride (1:1 using N-methoxy-N-methyl 2-chloro-benzamide instead of N-methoxy-N-methyl benzamide in step c). M.p. 145° C., (decomp.).

MS m/e (%): 599.1 (M+H$^+$, 100).

EXAMPLE 13

2-Phenoxy-benzoic acid 3,5-bis-trifluoromethyl-benzyl Ester

To a solution of 118 mg (0.55 mmol) 2-phenoxybenzoic acid and 122 mg (0.50 mmol) 3,5 bis(trifluoromethyl)benzyl alcohol in 1.5 ml dichloromethane at 0° C. was added a solution of 124 mg (0.60 mmol) 1,3-dicyclohexylcarbodiimide and 7 mg (0.06 mmol) 4-dimethylaminopyridine in 1 ml dichloromethane. The ice bath was removed and stirring was continued at room temperature overnight. The solvent was removed in vacuo and the residue re-dissolved in diethyl ether, filtered and evaporated. The residue was purified by flash chromatography to give 70 mg (32%) of the title compound as white crystals.

MS m/e (%): 440 (M$^+$, 51), 347 (39), 227 (36), 197 (100).

EXAMPLE 14

2-Benzyl-N-(3,5-bis-trifluoromethyl-benzyl)-benzamide

To a solution of 255 mg (1.2 mmol) 2-benzylbenzoic acid in 1.5 ml tetrahydrofuran at 0° C. were added 195 mg (1.2 mmol) 1,1'-carbonyldiimidazole. After stirring for 2.5 h at room temperature, a solution of 243 mg (1.0 mmol) 3,5 bis(trifluoromethyl)benzylamine in 0.5 ml tetrahydrofuran was added and stirring was continued overnight. The solvent was removed in vacuo and the residue was purified by flash chromatography to give 210 mg (49%) of the title compound as white crystals.

MS m/e (%): 438 (M+H$^+$, 100).

EXAMPLE 15

2-Benzyl-N-(3,5-bis-trifluoromethyl-benzyl)-N-methyl-benzamide

To a solution of 100 mg (0.23 mmol) 2-benzyl-N-(3,5-bis-trifluoromethyl-benzyl)-benzamide in 1 ml N,N-dimethylformamide at 0° C. were added 50 mg (0.25 mmol) potassium hexamethyldisilazide. Stirring was continued for 1 h at this temperature and 0.016 ml (0.25 mmol) methyl iodide were added. After stirring for 3 h at room temperature, ethyl acetate was added. The mixture was washed with brine, dried (magnesium sulfate) and evaporated. The solvent was removed in vacuo and the residue was purified by flash chromatography to give 90 mg (87%) of the title compound as a colourless oil.

MS m/e (%): 452 (M+H$^+$, 100).

EXAMPLE 16

N-(3,5-Bis-trifluoromethyl-benzyl)-N-methyl-2(methyl-phenyl-amino)-benzamide a) N-(3,5-Bis-trifluoromethyl-benzyl)-2-phenylamino-benzamide The title compound was obtained as white crystals in comparable yield according to the procedure described above for the preparation of 2-benzyl-N-(3,5-bis-trifluoromethyl-benzyl)-benzamide.

MS m/e (%): 477 (M+K$^+$, 24), 461 (M+Na$^+$, 40), 439 (M+H$^+$, 100).

b) 2-Benzyl-N-(3,5-bis-trifluoromethyl-benzyl)-N-methyl-benzamide

The title compound was obtained as a colourless oil in comparable yield according to the procedure described above for the preparation of 2-benzyl-N-(3,5-bis-trifluoromethyl-benzyl)-N-methyl-benzamide.

MS m/e (%): 505 (M+K$^+$, 12), 489 (M+Na$^+$, 19), 467 (M+H$^+$, 100).

EXAMPLE 17

N-(2-Benzenesulfonyl-phenyl)-2-(3,5-bis-trifluoromethyl-phenyl)-N-methyl-isobutyramide a) N-(2-Benzenesulfonyl-phenyl)-2-(3,5-bis-trifluoromethyl-phenyl)-isobutyramide A solution of 233 mg (1.0 mmol) 2-aminophenyl phenyl sulfone and 0.25 ml (1.5 mmol) N-ethyldiisopropylamine in 2 ml dichloromethane was cooled in an ice bath and a solution of 350 mg (1.1 mmol) 2-(3,5-bis-trifluoromethyl-phenyl)-2-methyl-propionyl chloride in 1 ml dichloromethane was added dropwise. The reaction mixture was stirred at room temperature overnight, evaporated and the residue was purified by flash chromatography to give 490 mg (95%) of the title compound as a pale yellow oil.

MS m/e (%): 533 (M+NH$_4^+$, 60), 516 (M+H$^+$, 100).

b) N-(2-Benzenesulfonyl-phenyl)-2-(3,5-bis-trifluoromethyl-phenyl)-N-methyl-isobutyramide The title compound was obtained as a colourless oil in comparable yield according to the procedure described above for the preparation of 2-benzyl-N-(3,5-bis-trifluoromethyl-benzyl)-N-methyl-benzamide.

MS m/e (%): 552 (M+Na$^+$, 40), 530 (M+H$^+$, 100).

EXAMPLE 18

2-(3,5-Bis-trifluoromethyl-phenyl)-N-methyl-N-(2-phenoxy-phenyl)-isobutyramide

The title compound was obtained as a colourless oil in comparable yield according to the procedures described above for the preparation of N-(2-benzenesulfonyl-phenyl)-2-(3,5-bis-trifluoromethyl-phenyl)-N-methyl-isobutyramide using 2-phenoxyaniline instead of 2-aminophenyl phenyl sulfone.

MS m/e (%): 482 (M+H$^+$, 100).

EXAMPLE 19

N-(2-Benzyl-phenyl)-2-(3,5-bis-trifluoromethyl-phenyl)-N-methyl-isobutyramide

The title compound was obtained as a colourless oil in comparable yield according to the procedures described above for the preparation of N-(2-benzenesulfonyl-phenyl)-2-(3,5-bis-trifluoromethyl-phenyl)-N-methyl-isobutyramide using 2-benzylaniline instead of 2-aminophenyl phenyl sulfone.

MS m/e (%): 480 (M+H$^+$, 100).

EXAMPLE 20

2-(3,5-Bis-trifluoromethyl-phenyl)-N-methyl-N-(2-o-tolyloxy-phenyl)-isobutyramide The title compound was obtained as pale yellow crystals in comparable yield according to the procedures described above for the preparation of N-(2-benzenesulfonyl-phenyl)-2-(3,5-bis-trifluoromethyl-phenyl)-N-methyl-isobutyramide using 2-(o-tolyloxy)aniline instead of 2-aminophenyl phenyl sulfone.

MS m/e (%): 496 (M+H$^+$, 100).

EXAMPLE 21

N-(2-Benzoyl-phenyl)-2-(3,5-bis-trifluoromethyl-phenyl)-N-methyl-isobutyramide

The title compound was obtained as a pale yellow oil in comparable yield according to the procedures described above for the preparation of N-(2-benzenesulfonyl-phenyl)-2-(3,5-bis-trifluoromethyl-phenyl)-N-methyl-isobutyramide using 2-aminobenzophenone instead of 2-aminophenyl phenyl sulfone.

MS m/e (%): 516 (M+Na$^+$, 55), 494 (M+H$^+$, 100).

EXAMPLE 22

2-(3,5-Bis-trifluoromethyl-phenyl)-N-[2-(2,4-dichloro-phenoxy)-phenyl]-N-methyl-isobutyramide The title compound was obtained as a colourless foam in comparable yield according to the procedures described above for the preparation of N-(2-benzenesulfonyl-phenyl)-2-(3,5-bis-trifluoromethyl-phenyl)-N-methyl-isobutyramide using 2-(2,4-dichlorophenoxy)aniline instead of 2-aminophenyl phenyl sulfone.

MS m/e (%): 549 (M$^+$, 4), 530 (21), 388 (100).

EXAMPLE 23

2-(3,5-Bis-trifluoromethyl-phenyl)-N-(2-phenylsulfanyl-phenyl)-isobutyramide

The title compound was obtained as a pale yellow oil in comparable yield according to the procedure described above for the preparation of N-(2-benzenesulfonyl-phenyl)-2-(3,5-bis-trifluoromethyl-phenyl)-N-methyl-isobutyramide using 2-aminophenyl phenyl sulfide instead of 2-aminophenyl phenyl sulfone. Step b) was not performed.

MS m/e (%): 484 (M+H$^+$, 100).

EXAMPLE 24

2-(3,5-Bis-trifluoromethyl-phenyl)-N-methyl-N-[2-(methyl-phenyl-amino)-phenyl]-propionamide a) 2-(3,5-Bis-trifluoromethyl-phenyl)-N-(2-phenylamino-phenyl)-acetamide To a solution of 545 mg (2.0 mmol) 3,5-bis(trifluoromethyl)phenylacetic acid in 2 ml tetrahydrofuran at 0° C. were added 325 mg (2.0 mmol) 1,1'-carbonyldiimidazole. After stirring for 2.5 h at room temperature, 305 mg (1.66 mmol) 2-aminodiphenylamine were added and stirring was continued for 8 h at 60° C. The solvent was removed in vacuo and the residue was purified by flash chromatography to give 480 mg (66%) of the title compound as white crystals.

MS m/e (%): 439 (M+H$^+$, 35), 142 (100).

b) 2-(3,5-Bis-trifluoromethyl-phenyl)-N-methyl-N-[2-(methyl-phenyl-amino)-phenyl]-propionamide To a solution of 389 mg (0.89 mmol) 2-(3,5-bis-trifluoromethyl-phenyl)-N-(2-phenylamino-phenyl)-acetamide in 1 ml N,N-dimethylformamide at 0°C. were added 560 mg (2.66 mmol) potassium hexamethyldisilazide. Stirring was continued for 1 h at this temperature and 510 mg (2.66 mmol) methyl iodide were added. After stirring for 3 h at room temperature, ethyl acetate was added. The mixture was washed with brine, dried (magnesium sulfate) and evaporated. The solvent was removed in vacuo and the residue was purified by flash chromatography to give 110 mg (25%) of the title compound as white crystals.

MS m/e (%): 480 (M$^+$, 76), 239 (100).

EXAMPLE 25

2-(3,5-Bis-trifluoromethyl-phenyl)-N-methyl-N-[2-(methyl-phenyl-amino)-phenyl]-isobutyramide To a solution of 52 mg (0.11 mmol) 2-(3,5-bis-trifluoromethyl-phenyl)-N-methyl-N-[2-(methyl-phenyl-amino)-phenyl]-propionamide in 0.5 ml N,N-dimethylformamide at 0° C. were added 32 mg (0.16 mmol) potassium hexamethyldisilazide. Stirring was continued for 1 h at this temperature and 30 mg (0.16 mmol) methyl iodide were added. After stirring for 3 h at room temperature, ethyl acetate was added. The mixture was washed with brine, dried (magnesium sulfate) and evaporated. The solvent was removed in vacuo and the residue was purified by flash chromatography to give 54 mg (quantitative) of the title compound as colourless oil.

MS m/e (%): 494 (M+, 87), 195 (100).

EXAMPLE 26
2-(3,5-Bis-trifluoromethyl-phenyl)-N-[2-(methyl-phenyl-amino)-phenyl]-acetamide The title compound was obtained as white crystals in comparable yield according to the procedure described above for the preparation of 2-(3,5-bis-trifluoromethyl-phenyl)-N-methyl-N-[2-(methyl-phenyl-amino)-phenyl]-propionamide using N-methyl-N-phenyl-benzene-1,2-diamine instead of 2-aminodiphenylamine. Step b) was not performed.

MS m/e (%): 453 (M+H+, 100).

EXAMPLE 27
2-(3,5-Bis-trifluoromethyl-phenyl)-N-methyl-N-[2-(methyl-phenyl-amino)-phenyl]-acetamide The title compound was obtained as a colourless oil in comparable yield according to the procedure described above for the preparation of 2-(3,5-bis-trifluoromethyl-phenyl)-N-methyl-N-[2-(methyl-phenyl-amino)-phenyl]-propionamide using N,N'-dimethyl-N-phenyl-benzene-1,2-diamine instead of 2-aminodiphenylamine. Step b) was not performed.

MS m/e (%): 467 (M+H+, 100).

EXAMPLE 28
N-(3,5-Bis-trifluoromethyl-benzyl)-N-methyl-6-morpholin-4-yl-4-phenoxy-nicotinamide a) 6-Chloro-4-phenoxy-nicotinic Acid Ethyl Ester To a solution of 196 mg (ca. 4 mmol) sodium hydride dispersion in mineral oil (ca. 50%) in 15 ml N,N-dimethylformamide a solution of 385 mg (4.09 mmol) phenol in 10 ml N,N-dimethylformamide was added dropwise at room temperature under argon. After 15 min. this solution was slowly added via cannula to a solution of 4,6-dichloro-nicotinic acid ethyl ester in 20 ml N,N-dimethylformamide at room temperature. After 2 h the reaction was quenched with 20 ml water. The mixture was extracted with 3 50-ml portions of ethyl acetate. The combined organic extracts were dried with sodium sulfate and concentrated. After drying in high vacuo at 50° C. and flash column chromatography 800 mg (70.4%) of the title compound was obtained as a white solid. As a side product 130 mg (11.4%) 4-chloro-6-phenoxy-nicotinic acid ethyl ester were also isolated.

MS m/e (%): 277 (M+, 81), 232 ([M-OEt]+, 100).

b) 6-Morpholin-4-yl-4-phenoxy-nicotinic Acid Ethyl Ester

A solution of 130 mg (0.468 mmol) 6-chloro-4-phenoxy-nicotinic acid ethyl ester, 0.040 ml (0.47 mmol) morpholine and 0.065 ml (0.47 mmol) triethylamine in 7 ml tetrahydrofuran was stirred at reflux for 40 h. After cooling to room temperature the reaction mixture was filtered, diluted with ethyl acetate and washed with water and saturated aqueous sodium chloride solution. The organic layer was dried with sodium sulfate and concentrated. Flash column chromatography afforded 66 mg (43%) of the title compound as a white solid.

MS m/e (%): 329 (M+H+, 100).

c) 6-Morpholin-4-yl-4-phenoxy-nicotinic Acid

A mixture of 66 mg (0.20 mmol) 6-morpholin-4-yl-4-phenoxy-nicotinic acid ethyl ester, 2 ml methanol and 2 ml 1N aqueous sodium hydroxide solution was stirred at room temperature for 1 h. The reaction mixture was diluted with water and washed with tert-butyl-methyl-ether. The aqueous layer was acidified to pH 4–5 with concentrated hydrochloric acid solution and extracted with 3 portions of dichloromethane. The combined organic layers were washed with saturated aqueous sodium chloride solution and dried with sodium sulfate. Concentration afforded 46 mg (77%) of the title compound as a white solid.

MS m/e (%): 301 (M+H+, 100).

d) N-(3,5-Bis-trifluoromethyl-benzyl)-N-methyl-6-morpholin-4-yl-4-phenoxy-nicotinamide A mixture of 46 mg (0.15 mmol) 6-morpholin-4-yl-4-phenoxy-nicotinic acid, 43 mg (0.17 mmol) (3,5-bis-trifluoromethyl-benzyl)-methylamine, 32 mg (0.17 mmol) 1-(3-diaminopropyl)-3-ethyl-carbodiimide hydrochloride and a catalytic amount of 4-(N,N-dimethylamino)-pyridine in 3 ml dichloromethane was stirred at room temperature over night. The reaction mixture was diluted with water, adjusted to pH 6 with saturated aqueous ammonium chloride solution and extracted with dichloromethane. The combined organic layers were washed with saturated aqueous sodium chloride solution, dried with sodium sulfate and concentrated. Flash column chromatography afforded 68 mg (83%) of the title compound as a white solid.

MS m/e (%): 540 (M+H+, 100).

EXAMPLE 29
N-(3,5-Bis-trifluoromethyl-benzyl)-4-(2-chloro-phenoxy)-N-methyl-6-morpholin-4-yl-nicotinamide The title compound was obtained as a white solid in comparable yields according to the procedures described above for the preparation of N-(3,5-bis-trifluoromethyl-benzyl)-N-methyl-6-morpholin-4-yl-4-phenoxy-nicotinamide (Example 28) using 2-chlorophenol instead of phenol in step a).

MS m/e (%): 574 (M+H+, 100).

EXAMPLE 30
N-(3,5-Bis-trifluoromethyl-benzyl)-4-(2-chloro-phenoxy)-N-methyl-6-(4-methyl-piperazin-1-yl)-nicotinamide The title compound was obtained as a white solid in comparable yields according to the procedures described above for the preparation of N-(3,5-bis-trifluoromethyl-benzyl)-N-methyl-6-morpholin-4-yl-4-phenoxy-nicotinamide (Example 28) using 2-chlorophenol instead of phenol in step a) and 1-methylpiperazine instead of morpholine in step b).

MS m/e (%): 587 (M+H+, 100).

EXAMPLE 31
N-(3,5-Bis-trifluoromethyl-benzyl)-N-methyl-6-morpholin-4-yl-4-o-tolyloxy-nicotinamide The title compound was obtained as a white solid in comparable yields according to the procedures described above for the preparation N-(3,5-bis-trifluoromethyl-benzyl)-N-methyl-6-morpholin-4-yl-4-phenoxy-nicotinamide (Example 28) using o-cresol instead of phenol in step a).

MS m/e (%): 554 (M+H+, 100).

Table 1 sets for the the subtituents for each compound of the previously described Examples.

TABLE 1

| Example No. | R | R¹ | R² | R³ | X | Y | R⁴ | Z |
|---|---|---|---|---|---|---|---|---|
| 1 | H | H | 3,5-CF₃ | CH₃/CH₃ | —N(CH₃)C(O)— | —C(O)— | H | =N— |
| 2 | H | H | 3,5-CF₃ | CH₃/CH₃ | —N(CH₃)C(O)— | —C(O)— | 4-Cl | —CH= |
| 3 | H | H | 3,5-CF₃ | CH₃/CH₃ | —N(CH₃)C(O)— | —C(O)— | H | —CHCH₃— |
| 4 | H | H | 3,5-CF₃ | CH₃/CH₃ | —N(CH₃)C(O)— | —C(O)— | 3-Cl | —CH= |
| 5 | H | 3-Cl | 3,5-CF₃ | CH₃/CH₃ | —N(CH₃)C(O)— | —C(O)— | H | —CH= |
| 6 | H | H | 3,5-CF₃ | CH₃/CH₃ | —N(CH₃)C(O)— | —C(O)— | 6-OCH₃ | —CH= |
| 7 | H | H | 3,5-CF₃ | CH₃/CH₃ | —N(CH₃)C(O)— | —C(O)— | 4-OCH₃ | —CH= |
| 8 | Cl | H | 3,5-CF₃ | H/CH₃ | —N(CH₃)C(O)— | —S— | 4-Cl | —CH= |
| 9 | H | H | 3,5-CF₃ | H/CH₃ | —N(CH₃)C(O)— | —C(O)— | 4-Cl | —CH= |
| 10 | H | H | 3,5-CF₃ | CH₃/CH₃ | —NH—C(O)— | —C(O)— | 4-methylpiperazin-1-yl | —CH= |
| 11 | H | H | 3,5-CF₃ | H/H | —C(O)—N(CH₃)— | —C(O)— | 4-methylpiperazin-1-yl | —N= |
| 12 | Cl | H | 3,5-CF₃ | H/H | —C(O)—N(CH₃)— | —C(O)— | 4-methylpiperazin-1-yl | —N= |
| 13 | H | H | 3,5-CF₃ | H/H | —C(O)—O— | —O— | H | —CH= |
| 14 | H | H | 3,5-CF₃ | H/H | —C(O)—NH— | —CH₂— | H | —CH= |
| 15 | H | H | 3,5-CF₃ | H/H | —C(O)—N(CH₃)— | —CH₂— | H | —CH= |
| 16 | H | H | 3,5-CF₃ | H/H | —C(O)—N(CH₃)— | —N(CH₃)— | H | —CH= |
| 17 | H | H | 3,5-CF₃ | CH₃/CH₃ | —N(CH₃)C(O)— | —S(O)₂— | H | —CH= |
| 18 | H | H | 3,5-CF₃ | CH₃/CH₃ | —N(CH₃)C(O)— | —O— | H | —CH= |
| 19 | H | H | 3,5-CF₃ | CH₃/CH₃ | —N(CH₃)C(O)— | —CH₂— | H | —CH= |
| 20 | CH₃ | H | 3,5-CF₃ | CH₃/CH₃ | —N(CH₃)C(O)— | —O— | H | —CH= |
| 21 | H | H | 3,5-CF₃ | CH₃/CH₃ | —N(CH₃)C(O)— | —C(O)— | H | —CH= |
| 22 | Cl | 4-Cl | 3,5-CF₃ | CH₃/CH₃ | —N(CH₃)C(O)— | —O— | H | —CH= |
| 23 | H | H | 3,5-CF₃ | CH₃/CH₃ | —NH—C(O)— | —S— | H | —CH= |
| 24 | H | H | 3,5-CF₃ | CH₃/H | —N(CH₃)C(O)— | —N(CH₃)— | H | —CH= |
| 25 | H | H | 3,5-CF₃ | CH₃/CH₃ | —N(CH₃)C(O)— | —N(CH₃)— | H | —CH= |
| 26 | H | H | 3,5-CF₃ | H/H | —NH—C(O)— | —N(CH₃)— | H | —CH= |
| 27 | H | H | 3,5-CF₃ | H/H | —N(CH₃)C(O)— | —N(CH₃)— | H | —CH= |
| 28 | H | H | 3,5-CF₃ | H/H | —C(O)—N(CH₃)— | —O— | 4-methylmorpholin-1-yl | —N= |
| 29 | H | 2-Cl | 3,5-CF₃ | H/H | —C(O)—N(CH₃)— | —O— | 4-methylmorpholin-1-yl | —N= |
| 30 | H | 2-Cl | 3,5-CF₃ | H/H | —C(O)—N(CH₃)— | —O— | 4-methylpiperazin-1-yl | —N= |
| 31 | H | 2-CH₃ | 3,5-CF₃ | H/H | —C(O)—N(CH₃)— | —O— | 4-methylpiperazin-1-yl | —N= |

EXAMPLE A

Tablets of the following composition are manufactured in the usual manner:

|  | mg/tablet |
| --- | --- |
| Active substance | 5 |
| Lactose | 45 |
| Corn Starch | 15 |
| Microcrystalline cellulose | 34 |
| Magnesium stearat | 1 |
| Tablet weight: | 100 |

EXAMPLE B

Capsules of the following composition are manufactured:

|  | mg/capsule |
| --- | --- |
| Active substance | 10 |
| Lactose | 155 |
| Corn starch | 30 |
| Talc | 5 |
| Capsule fill weight: | 200 |

The active substance, lactose and corn starch are firstly mixed in a mixer and then in a comminuting machine. The mixture is returned to the mixer, the talc is added thereto and mixed thoroughly. The mixture is filled by machine into hard gelatine capsules.

EXAMPLE C

Suppositories of the following composition are manufactured:

|  | mg/supp. |
| --- | --- |
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

What is claimed is:

1. A compound of the general formula

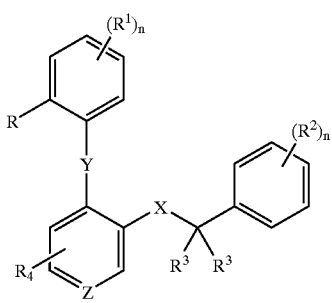

I wherein

R is hydrogen, lower alkyl, lower alkoxy, halogen or trifluoromethyl;

$R^1$ is hydrogen or halogen; or

R and $R^1$ may be together —CH=CH—CH=CH—; $R^2$ is hydrogen, halogen, trifluoromethyl, lower alkoxy or cyano;

$R^3$ is independently from each other hydrogen, lower alkyl or form a cycloalkyl group;

$R^4$ is hydrogen, halogen, lower alkyl, or lower alkoxy;

$R^5$ is, independently from each other, hydrogen, $C_{3-6}$-cycloalkyl, benzyl or lower alkyl;

X is —$N(R^5)C(O)$;

Y is —O—, —S—, or —$SO_2$;

Z is —CH= or —C(Cl)=; and n is 0–4;

and pharmaceutically acceptable acid addition salts thereof.

2. A compound according to claim 1, wherein Y is —O—, and $R^4$ is hydrogen.

3. A compound according to claim 2, 2-(3,5-Bis-trifluoromethyl-phenyl)-N-methyl-N-(2-phenoxy-phenyl)-isobutyramide.

4. A compound according to claim 2, 2-(3,5-Bis-trifluoromethyl-phenyl)-N-methyl-N-(2-o-tolyloxy-phenyl)-isobutyramide.

5. A compound according to claim 2, 2-(3,5-Bis-trifluoromethyl-phenyl)-N-[2-(2,4-dichloro-phenoxy)-phenyl]-N-methyl-isobutyramide.

6. A pharmaceutical composition comprising:

a compound of the following formula I

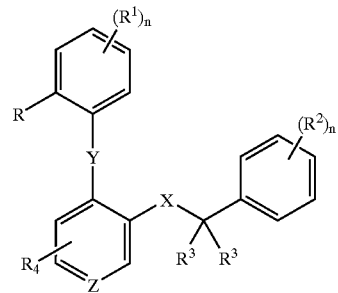

I wherein

R is hydrogen, lower alkyl, lower alkoxy, halogen or trifluoromethyl;

$R^1$ is hydrogen or halogen; or

R and $R^1$ may be together —CH=CH—CH=CH—;

$R^2$ is hydrogen, halogen, trifluoromethyl, lower alkoxy or cyano;

$R^3$ is independently from each other hydrogen, lower alkyl or form a cycloalkyl group;

$R^4$ is hydrogen, halogen, lower alkyl, or lower alkoxy;

$R^5$ is, independently from each other, hydrogen, $C_{3-6}$-cycloalkyl, benzyl or lower alkyl;

X is —$N(R^5)C(O)$;

Y is —O—, —S—, or —$SO_2$—;

Z is —CH= or —C(Cl)=; and n is 0–4;

and pharmaceutically acceptable acid addition salts thereof; and a pharmaceutically acceptable carrier or excipient.

7. A method of treating a disease mediated by modulation of the Neurokinin 1 receptor comprising administering, to a patient in need thereof, a therapeutically effective amount of a compound of formula I

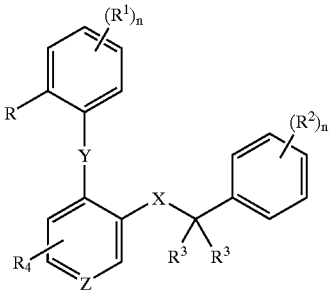

wherein
R is hydrogen, lower alkyl, lower alkoxy, halogen or trifluoromethyl;
$R^1$ is hydrogen or halogen; or
R and $R^1$ may be together —CH=CH—CH=CH—;
$R^2$ is hydrogen, halogen, trifluoromethyl, lower alkoxy or cyano;
$R^3$ is independently from each other hydrogen, lower alkyl or form a cycloalkyl group;
$R^4$ is hydrogen, halogen, lower alkyl, or lower alkoxy;
$R^5$ is, independently from each other, hydrogen, $C_{3-6}$-cycloalkyl, benzyl or lower alkyl;
X is —N($R^5$)C(O);
Y is —O—, —S—, or —SO$_2$—;
Z is —CH= or —C(Cl)=; and
n is 0–4;
and pharmaceutically acceptable acid addition salts thereof.

* * * * *